United States Patent [19]
Li et al.

[11] Patent Number: 5,195,946
[45] Date of Patent: Mar. 23, 1993

[54] STABLE CATALYTIC AND AQUA-ACTIVATED POLYURETHANE CASTING BANDAGE

[75] Inventors: Hai-sheng Li, Shanghai; Jia-ju Fan, Huangyan, both of

[73] Assignees: Zhejiang Province Science & Technology Development Corp., Huangyan, China; Huangyan Medical Treatment Material Factory, China

[21] Appl. No.: 758,827

[22] Filed: Sep. 12, 1991

[30] Foreign Application Priority Data

Sep. 15, 1990 [CN] China ................ 90102934.3

[51] Int. Cl.⁵ ..................................... A61F 5/04
[52] U.S. Cl. ........................... 602/8; 523/105; 428/290; 428/913; 521/115; 528/53
[58] Field of Search ................ 602/8; 523/105; 428/273, 290, 913; 521/115; 528/53

[56] References Cited

U.S. PATENT DOCUMENTS

| | | |
|---|---|---|
| 3,421,501 | 1/1969 | Beightol . |
| 3,645,925 | 2/1972 | Speranza et al. . |
| 3,881,473 | 5/1975 | Corvi et al. . |
| 4,105,025 | 8/1978 | Wang et al. . |
| 4,228,248 | 10/1980 | Zimmerman ............... 521/115 |
| 4,273,885 | 6/1981 | Dominguez et al. . |
| 4,376,438 | 3/1983 | Straube et al. . |
| 4,427,002 | 1/1984 | Baron et al. . |
| 4,433,680 | 2/1984 | Yoon . |
| 4,502,479 | 3/1985 | Garwood et al. . |
| 4,574,793 | 3/1986 | Lee et al. . |
| 4,705,840 | 11/1987 | Buckanin . |
| 5,086,151 | 2/1992 | Ito et al. .................... 528/53 |

FOREIGN PATENT DOCUMENTS 89103603.2  5/1990  China .

*Primary Examiner*—Paul Prebilic
*Attorney, Agent, or Firm*—Finnegan, Henderson, Farabow, Garrett & Dunner

[57] ABSTRACT

The invention is directed to a stable catalytic and aqua-activated polyurethane bandage used for orthopedic casting. The bandage has a substrate and an aqua-activated polyurethane prepolymer. The catalyst used to make the prepolymer is α-(morpholinopolyethoxy)-β-morpholinoethane or the mixture of α-(morpholinopolyethoxy)-β-morpholinoethane and cocatalyst bis-(2-dimethylaminoethyl) ether. The catalyst in this bandage can be optionally combined with a stabilizing agent, such as ethane-sulfonic acid to form a structurally stable complex. The catalyst of this invention provides an excellent solidification time and significantly prolongs the storage period of the bandage.

11 Claims, 1 Drawing Sheet

STABLE CATALYTIC AND AQUA-ACTIVATED POLYURETHANE CASTING BANDAGE

FIELD OF THE INVENTION

This invention discloses a kind of casting type bandage, and more specifically, relates to a modified aqua-activated polyurethane orthopedic bandage used for orthopedia in the department of orthopedics and as a medicinal material for fixing of fractures. It can be stably stored.

BACKGROUND OF THE INVENTION

The gypsum bandage for fixing extremities has existed for a long time. This bandage is formed by sedimentation of gypsum powder onto a cotton gauze. It is cast and hardened after impregnating with water. However, there are a series of drawbacks existing in the plaster bandage, such as bulkiness, a tendency to crack, poor air permeability, softening or breaking by soaking in water, and poor penetration of X-rays. Furthermore, the X-ray examination is taken after the patient has been fitted with the plaster bandage, and so, the condition of the fracture can't be observed clearly.

In order to overcome these drawbacks of plaster bandages, bandages prepared from high-molecular weight synthetic materials instead of plaster have been used.

U.S. Pat. Nos. 3,421,501 and 3,881,473 disclose that the substrate of a bandage is made of soft fibers. It is impregnated with a type of light-sensitive resin on its surface which can be solidified by means of ultraviolet light. But bulky hardening equipment is required; the operation is very inconvenient; and at the same time, the time required for solidification and conforming the bandage to the body part is too long. These drawbacks are a large limitation to practical usage.

U.S. Pat. No. 4,105,025 discloses a kind of thermoplastic bandage composed of high molecular weight materials. When the bandage is heated above its melting point of 77°-82° C., it can be wound, thereby surrounding the therapeutic position of the patient, and then it can solidify after cooling. Of course, it can be seen that the patient's skin has to withstand this temperature during winding, and the burning of the skin can be very severe.

In recent times, U.S. Pat. Nos. 4,376,438; 4,502,479, 4,427,002 and Faming Zhuanli (Chinese Patent Applications) CN 89103603,2 disclose subsequently applying aqua-activated polyurethane prepolymer as the material for an orthopedic bandage. The major components of this prepolymer are the reaction products of isocyanate and polyhydric alcohol. The method for application of this bandage is the same as that of the plaster bandage.

It can be bandaged on a patient's extremity after it is impregnated with water. The prepolymer can be polymerized when combining with water, i.e., the polymer is solidified to a rigid state, thus fixing it to the patient. In order to make the bandage solidify or harden quickly in about 10 minutes, it is necessary to blend in a certain amount of catalyst.

U.S. Pat. No. 4,376,438 discloses that aminopolyhydric alcohol is used as a catalyst. U.S. Pat. No. 4,427,002 discloses A-99, i.e., bis-(2-dimethylamino ethyl) ether, as a catalyst for controlling the time of solidification. U.S. Pat. No. 4,502,479 discloses that DMEA (dimethyl ethanol amine) or the mixture of DMEA and A-99, i.e., bis-(2-dimethylamino ethyl) ether, can be used as catalyst. Faming Zhuanli CN 89103603,2 discloses a mixture of DMEA and anhydrous $K_2CO_3$ can be used as a mixed catalytic system.

However, the tertiary amine catalyst presented within the polyurethane bandage as above incurs gelatinizing side reactions in the prepolymer. These side reactions may form biuret or ureido formate and a small amount of trimer of isocyanate. The gelatin caused by these side reactions can cause the bandage to solidify or harden prematurely before use. Thus, the storage period of the bandage is too short and its stability is poor. Generally, the storage period of the bandage is only about 12 months at ambient temperature (23° C.), and those bandages can't be made commercially available. Although many catalysts have been used to catalyze the reaction of the isocyanate moiety of polyurethane prepolymer with water, there is little use for them in the orthopedic bandage of the casting type because these catalysts can,t provide a long storage period for the orthopedic bandage.

U.S. Pat. No. 4,433,680 (Johnson & Johnson, Inc.) discloses the catalyst DMDEE, i.e., bis-(2-morpholino diethyl) ether, applied previously to the forming of polyurethane foams (U.S. Pat. No. 3,645,925) and to the forming of polyurethane injection molding elastomer (U.S. Pat. No. 4,273,885). It is used polyurethane prepolymer in the orthopedic bandage. Not only is the storage period of the bandage prolonged, but there is excellent time of solidification. Thus, this modification develops an excellent prospect for wide application of the aqua-activated polyurethane bandage.

Thereafter, U.S. Pat. No. 4,574,793 (Hexcel Co.) applied bis-(2,6-dimethylmorpholinoethyl) ether and U.S. Pat. No. 4,705,840 (3M & Co.) synthesized by itself MEMP, i.e., 4[2-methyl-2-(4-morpholino ethoxy)-ethane-] morpholine, and used it as the catalyst of the polyurethane prepolymer in the orthopedic bandage. The same effect occurred, i.e., the storage period was prolonged and satisfactory results were obtained.

OBJECT OF THE INVENTION

An object of the present invention is to provide a casting type bandage with excellent storage stability and aqua-activity.

SUMMARY OF THE INVENTION

In the present invention, a special catalyst has been used. The inventors have synthesized a novel compound with bismorpholine structure, specifically, LF-3, i.e., α-(morpholino polyethoxy)-β-morpholino ethane. The chemical structural formula is as follows:

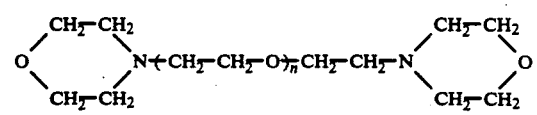

wherein n=2−8.

The present invention is further directed to a stable catalytic and aqua-activated polyurethane bandage comprising a woven glass fiber or synthetic fiber substrate coated with an aqua-activated polyurethane prepolymer, said prepolymer comprising an aromatic isocyante, a polyhydroxy compound, and a catalyst, wherein the equivalent ratio of NCO:OH in the prepolymer is from 3:1 to 9:1, and said catalyst is α-(morpholinopolyethoxy)-β-morpholinoethane or a mixture of α-(morpholinopolyethoxy)-β-morpholinoethane and a cocatalyst of bis-(2-dimethylaminoethyl) ether.

DETAILED DESCRIPTION OF THE INVENTION

Figure 1:
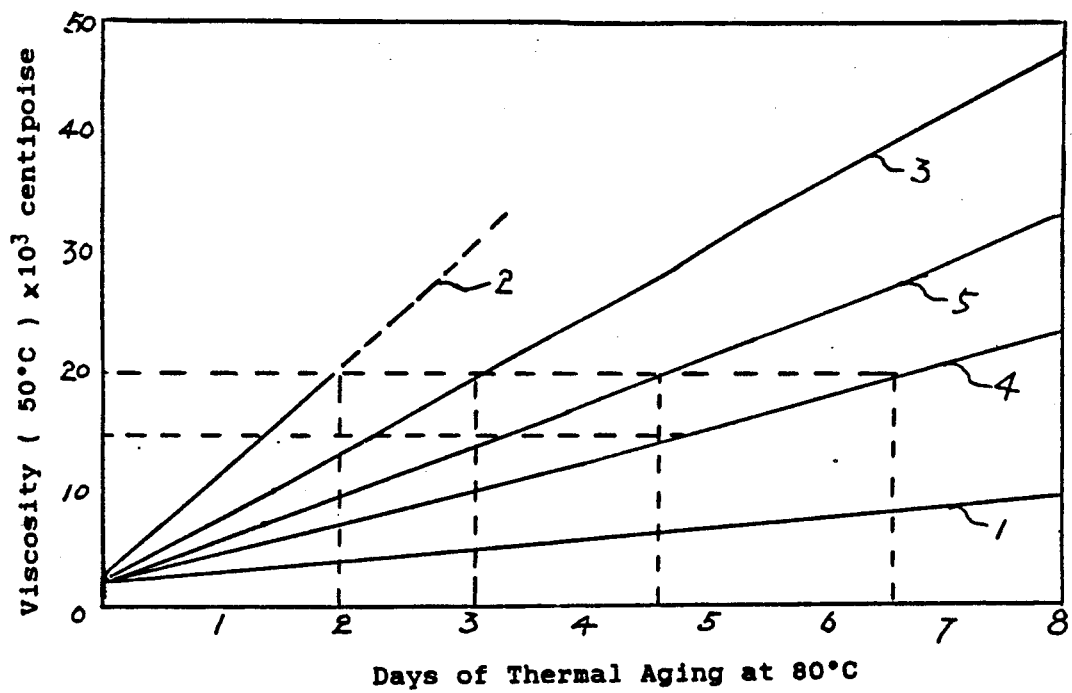

LF-3 is used as the catalyst for the aqua-activated polyurethane prepolymer. The rate of formation of side reactions is quite lower than that of the application of tertiary amine catalyst.

Furthermore, a suitable amount of stabilizing agent, such as methane sulfonic acid, can be added into the prepolymer to form a stable complex with the catalyst LF-3. The storage period or storage stability of the bandage prepared from the stable catalytic polyurethane prepolymer of this invention can be increased from 1.5 to 2-fold over that of a bandage prepared by utilizing a tertiary amine as the catalytic system. But as for this premise, the solidification time required in clinics must be guaranteed.

The aromatic isocyanates in the stable catalytic and aqua-activated polyurethane prepolymer of this invention can be any kind of aromatic isocyanate described in polyurethane chemistry, e.g., as described by Chemistry and Technology of Polyurethane, published by Intersciences Co., 1962.

The aromatic isocyanates comprise toluene diisocyanate (TDI), diphenyl methane-diisocyanate (MDI) or carbodiimide [—C(=NH)$_2$]group-containing modified liquid MDI.

The polyhydroxy compound used in the polyurethane prepolymer of this invention is a mixture of dihydroxy polyether and trihydroxy polyether, with a mol. wt. of 400–2000. The equivalent ratio of the dihydroxy group to trihydroxy group is from 1:9 to 9:1, and the ratio of NCO:OH in the prepolymer is from 2:1 to 10:1 The NCO content is 5%–10%.

The content of LF-3, i.e., α-(morpholino polyethoxy)-β-morpholino ethane, catalyst in the stable catalytic and aqua-activated polyurethane prepolymer of this invention based on the total weight of the prepolymer is 0.1–10% preferably in the range of 1.0–10%, most preferably in the range of 1.0–4.0%. A small amount of cocatalyst A-99, i.e., bis-(2-dimethylaminoethyl) ether, may be utilized jointly with catalyst LF-3. Its content is 0.1% to 1.0%, more preferably 0.1 to 0.5%, by total weight of prepolymer.

The polyurethane prepolymer can otherwise comprise a small amount of a stabilizing agent of methane sulfonic acid in an amount of 0.01–0.5% and an antifoam agent in an amount of 0.01–1.0%. All of the percentages are based upon the total weight of the prepolymer. Small amounts of a thixotropic agent, antioxidant, thermal stabilizing agent, etc. may also be present.

The thixotropic agent can be, for example, silica white, preferably in an amount from 0.5 to 4.0% based on the total weight of the polyurethane prepolymer. The antioxidant can be, for example 2,6-ditertiarybutyl-4-ethylphenol, preferably in an amount from 0.01 to 0.1% based on the total weight of the polyurethane prepolymer. The heat stabilizer can be, for example, calcium stearate, preferably in an amount from 0.1 to 2.0% based on the total weight of the polyurethane prepolymer. The antifoam agent can be, for example, antifoam silicone oil 201, preferably in an amount from 0.1 to 2.0% based on the total weight of the polyurethane prepolymer.

The following Example is given to show the preparation of the stable catalytic and aqua-activated polyurethane prepolymer A.

EXAMPLE

Into a 5 liter reaction vessel, which is equipped with a thermometer, mechanical stirrer, liquid feeding equipment and N gas inlet, 3400 g of carbodiimide-containing, diphenyl-methanediisocyanate (liquid MDI), 135 g of methane-sulfonic acid, 54 g of antifoam silicone oil, 108 g of silica white and 16.2 g of 2.6-ditert-butyl-4-methyl phenol are added. The mixture is heated to 55° C. 1200 g of dihydroxy polyether (OH=105) and 800 g of trihydroxypolyether (OH=86) as a mixed polyhydroxyl compound are added dropwise. The temperature is controlled at 60°–65° C. The reaction proceeds for 1–2 hrs. After cooling the material is drawn and is ready for use. The resultant prepolymer viscosity is 2800 centipoise and has an NCO content=14.8%. 1.5% (wt.) of LF-3 catalyst or 1.0% of LF-3, i.e., α-(morpholino ethoxy-ethoxy) -β-morpholinoethane, and 0.1% of A-99 are added to this polyurethane prepolymer. This material is coated onto the woven substrate. After it is impregnated in water for 15 sec., the bandage is wound around the affected region of the patient. The times of solidification are 9 min. and 7 min. for 1.5% LF-3 and 1.0% LF-3/0.1% A-99, respectively.

The testing of the storage stability is performed as directed by U.S. Pat. No. 4,433,680. It is a good method for detecting storage stability by means of maintaining the polyurethane prepolymer at a definite temperature for accelerating aging. After the test-sample has undergone a definite time for aging, its viscosity is determined. A lower prepolymer viscosity indicates a better storage stability or that it can be stored over a longer storage period.

In accordance with U.S. Pat. No. 4,574,793 (Hexcel Co.), the storage stability of the polyurethane prepolymer was determined with different catalytic systems at 80° C. after undergoing a definite time for thermal aging. The distribution of viscosity was measured.

Testing method

The sample of polyurethane prepolymer A prepared in the above example is accurately weighed. A definite amount of catalyst is added. They are placed into a dry bag of Al-plastic complex foil and put into a dry box with protection under N. It is sealed after thorough agitation. This sample is then placed into an oven at a constant temperature of 80° C.

The sample is taken out at 24-hr intervals to determine its viscosity after cooling down to 50° C. The total test period runs for 7 days. The test results regarding the influence of different catalytic systems DMEA, A-99, LF-3 and LP3+A-99 on storage stabilities of polyurethane prepolymer are shown below in Table 1.

TABLE 1

Storage Stabilities of Polyurethane Prepolymer A (NCO 14.8%) with Different Catalytic Systems

| No. | catalyst (%) | time to solidification (min) | Viscosity in centipoise determined at 50° C. 80° C. thermal aging (days) | | | | | | | |
|---|---|---|---|---|---|---|---|---|---|---|
| | | | 0 | 1 | 2 | 3 | 4 | 5 | 6 | 7 |
| 1 | not added | | 3200 | 3000 | 3300 | 3300 | 4200 | 4600 | 5100 | 6000 |
| 2 | DMEA (1.5) | 9 | 4200 | 11000 | 20000 partially harden | | | | | |
| 3 | A-99 (0.35) | 8 | 3300 | 5700 | 12500 | 17000 | 22500 | 28500 | harden | |
| 4 | LF-3 (1.5) | 9 | 3500 | 4600 | 7000 | 9500 | 12500 | 15600 | 19500 | 20500 |
| 5 | LF-3(1.0) A-99 (0.1) | 7 | 3600 26500 | 3600 | 10500 | 14000 | 17500 | 20500 | 25600 | |

These data are plotted in FIG. 1 and indicate the distribution of viscosities during 80° C. thermal aging.

| curve | 1 | no catalyst is used. |
|---|---|---|
| curve | 2 | DMEA 1.5% |
| curve | 3 | A-99 0.35% |
| curve | 4 | LF-3 1.5% |
| curve | 5 | LF-3 1.0%; A-99 0.1% |

The polyurethane prepolymer with DMEA (1.5%) as catalyst has a storage period of about 12 months. We assumed the stability coefficient of the prepolymer with this catalyst system to be K=1, and then compared the stabilities of the prepolymers with other various catalystic systems. From FIG. 1, we can compute the days required for the viscosities of prepolymers with various catalytic systems to arrive at 15000 and 20000 centipoise respectively after an 80° C. thermal aging. These data are shown in tables 2 an d3, respectively.

TABLE 2

Time (days) Required for 80° C. Thermal Aging When the Viscosity (50° C.) of Prepolymer A with Various Catalytic Systems Reached 15000 Centipoise

| No. | Catalyst (%) | time to solidification (min) | stability coefficient (K) | days of thermal aging at 80° C. | storage period at 23° C. (months) |
|---|---|---|---|---|---|
| 1 | DMEA (1.5) | 9 | 1.0 | 1.5 | ~12 |
| 2 | A-99 (0.35) | 8 | 1.33 | 2.0 | ~16 |
| 3 | LF-3 (1.5) | 9 | 3.33 | 5.0 | ~40 |
| 4 | LF-3 (1.0) A-99 (0.1) | 7 | 2.33 | 3.5 | ~28 |

TABLE 3

Time (days) Required for 80° C. Thermal Aging When the Viscosity (50° C.) of Prepolymer A with Various Catalytic Systems Reached 20,000 Centipoise

| No. | Catalyst (%) | time to solidification (min) | stability coefficient K | days of thermal aging | storage period at 23° C. (months) |
|---|---|---|---|---|---|
| 1 | DMEA (1.5) | 9 | 1.0 | 2.0 | ~12 |
| 2 | A-99 (0.35) | 8 | 1.5 | 3.0 | ~18 |
| 3 | LF-3 (1.5) | 9 | 3.5 | 7.0 | ~42 |
| 4 | LF-3 (1.0) | 7 | 2.5 | 5.0 | ~30 |
| | A-99 (0.1) | | | | |

The above results indicate that when DMEA is used as the catalyst (its content is 1.5% of the total weigh of the prepolymer) in the polyurethane prepolymer A (NCO content=14.8%) prepared according to the Example above for this invention, the solidification time determined is 9 min. and the viscosity (50° C.) of the prepolymer reaches 15000 centipoise after 80° C. thermal aging for 1.5 days. We take the stability coefficient of K=1 as the storage stability index; that is, it is equivalent to a stable storage period at 23° C. of about 12 months.

If we take A-99 as the catalyst, wherein it: content is 0.35% of the total weight of the prepolymer, the solidification time determined is 8 min. and the viscosity of the prepolymer reaches 15000 centipoise after 80° C. thermal aging for 2. days. Its stability coefficient is K=3.33, which is equivalent to a stable storage period at 23° C. of about 16 months.

If we use the LF-3 of this invention as catalyst, wherein its content is 1.5% of the total weight of the prepolymer, the solidification time determined is 9 min. and the viscosity (50° C.) of the prepolymer reaches 15000 centipoise after 80° C. thermal aging for 5.0 days. Its stability coefficient i: K=3.33, which is equivalent to a stable storage period at ambient temp (23° C.) of 40 months. The storage stability is enhanced 2.3 fold as compared with that of the DMEA catalyzing system and is enhanced 1.5 fold as compared with the A-99 catalyzing system.

Furthermore, when the LF-3 catalyst and A-99 cocatalyst are used, their contents are 1.0% and 0.1% by total weight of the prepolymer, respectively. The solidification time determined is 7 min. and the viscosity (50° C.) of the prepolymer reaches 15000 centipoise after 80° C. thermal aging for 3.5 days. Its stability coefficient is K=2.33, which is equivalent to a stable storage period at ambient temp. (23° C.) of 28 months.

Similar results are shown in Table 3, wherein a prepolymer A with various catalytic systems is employed, but a viscosity (50° C.) of 20000 centipoise is used. The relation of time (days) for 80° C. thermal aging can be similarly measured as was done for Table 2.

Other features, advantages and embodiments of the invention disclosed herein will be readily apparent to those exercising ordinary skill after reading the foregoing disclosure. In this regard, while specific embodiments of the invention have been described in considerable detail, variations and modifications of these embodiments can be effected without departing from the spirit and scope of the invention as described and claimed herein.

What is claimed is:

1. A stable catalytic and aqua-activated polyurethane bandage comprising a woven glass fiber or synthetic fiber substrate coated with an aqua-active polyurethane prepolymer, said prepolymer comprising an aromatic isocyanate, a polyhydroxy compound, and a catalyst, wherein the equivalent ratio of NCO: OH in the prepolymer is from 3:1 to 9:1, and said catalyst is α-(morpholinopolyethoxy)-β-morpholinoethane or a mixture of α-(morpholinopolyethyoxy)-β-morpholinoethane and a cocatalyst of bis-(2-dimethylaminoethyl) ether.

2. The stable catalytic and aqua-activated polyurethane bandage according to claim 1, wherein said aromatic isocyanate is carbodiimide-containing diphenylmethane-diisocyanate.

3. The stable catalytic and aqua-activated polyurethane bandage according to claim 1, wherein said polyhydroxy compound is a mixture of dihydroxypolyether and trihydroxypolyether, wherein the ratio of the dihydroxy to trihydroxy is from 1:9 to 9:1, and the molecular weight is from 400 to 2000.

4. The stable catalytic and aqua-activated polyurethane bandage according to claim 1, wherein said catalyst is α-(morpholinopolyethoxy)-β-morpholinoethane having a structural formula I

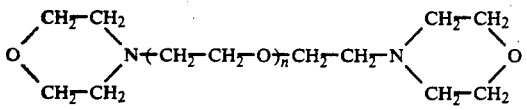

wherein n=2−8 and said catalyst is in a content of from 0.5 to 5.0%, based on the total weight of the polyurethane prepolymer.

5. The stable catalytic and aqua-activated polyurethane bandage according to claim 1, wherein said catalyst is a mixture of (a) α-(morpholinopolyethoxy)-β-morpholinoethane having a structural formula I

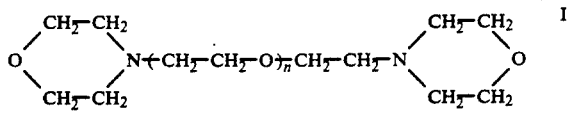

where n=2−8 and (b) cocatalyst bis-(2-dimethyl amino ethyl) ether, wherein component (a) is in a content of from 1.0 to 3.0%, and component (b) is in a content of from 0.1 to 0.5%, based on the total weight of the polyurethane prepolymer.

6. The stable catalytic and aqua-activated polyurethane bandage according to claim 1, wherein said prepolymer further comprises a stabilizer, a thixotropic agent, an antioxidant, a heat stabilizer or an anti-foam agent.

7. The stable catalytic and aqua-activated polyurethane bandage according to claim 6, wherein said stabilizer is methane-sulfonic acid in a content of from 0.01 to 0.5% based on the total weight of the polyurethane prepolymer.

8. The stable catalytic and aqua-activated polyurethane bandage according to claim 6, wherein said thixotropic agent is silica white in a content of from 0.5 to 4.0% based on the total weight of the polyurethane prepolymer.

9. The stable catalytic and aqua-activated polyurethane bandage according to claim 6, wherein said antioxidant is 2,6-ditertiarybutyl-4-ethylphenol in a content of from 0.01 to 0.1% based on the total weight of the polyurethane prepolymer.

10. The stable catalytic and aqua-activated polyurethane bandage according to claim 6, wherein said heat stabilizer is calcium stearate in a content of from 0.1 to 2.0% based on the total weight of the polyurethane prepolymer.

11. The stable catalytic and aqua-activated polyurethane bandage according to claim 6, wherein said antifoam agent is antifoam silicone oil in a content of from 0.1 to 1.0% based on the total weight of the polyurethane prepolymer.

* * * * *

UNITED STATES PATENT AND TRADEMARK OFFICE
CERTIFICATE OF CORRECTION

PATENT NO. : 5,195,946
DATED : MARCH 23, 1993
INVENTOR(S) : LI HAI-SHENG ET AL.

It is certified that error appears in the above-identified patent and that said Letters Patent is hereby corrected as shown below:

Title Page, line 2, after "both of", insert --China--.

Signed and Sealed this

Twenty-third Day of November, 1993

Attest:

BRUCE LEHMAN

*Attesting Officer*     *Commissioner of Patents and Trademarks*